United States Patent [19]

Bartelt et al.

[11] Patent Number: 5,063,929
[45] Date of Patent: Nov. 12, 1991

[54] ELECTRONIC STIMULATING DEVICE HAVING TIMED TREATMENT OF VARYING INTENSITY AND METHOD THEREFOR

[75] Inventors: James T. Bartelt, Longmont; Frank W. Harris, Boulder; Alan R. Owens, Longmont, all of Colo.

[73] Assignee: Staodyn, Inc., Longmont, Colo.

[21] Appl. No.: 398,734

[22] Filed: Aug. 25, 1989

[51] Int. Cl.$^5$ ............................................. A61N 1/18
[52] U.S. Cl. .................................. 128/421; 128/423 W
[58] Field of Search ........................ 128/421, 422, 423

[56] References Cited

U.S. PATENT DOCUMENTS

| | | | |
|---|---|---|---|
| 4,124,028 | 11/1978 | Gallo | 128/422 |
| 4,338,945 | 7/1982 | Kosugi et al. | 128/421 |
| 4,408,609 | 10/1983 | Axelgaard | 128/421 |
| 4,580,570 | 4/1986 | Sarrell et al. | 128/421 |
| 4,669,477 | 6/1987 | Ober | 128/421 |
| 4,782,837 | 11/1988 | Hogan | 128/421 |

Primary Examiner—William E. Kamm
Assistant Examiner—Scott M. Getzow
Attorney, Agent, or Firm—Robert E. Harris

[57] ABSTRACT

A device and method are disclosed for effecting timed treatment of varying intensity in an electronic stimulating device, with the stimulating device particularly illustrated being a transcutaneous nerve stimulating (TENS) device for effecting suppression of pain by nerve fiber stimulation. Biphasic constant current output pulses are applied to a user through electrode pairs noninvasively positioned at the skin of the user. Microprocessor generated control pulses control generation of the biphasic output pulses at a biphasic output stage associated with each electrode pair. Stimulation may be continuously applied at a level selected by the user or may be applied in timed varying intensities the maximum level of which is selectable, with a display also being provided of selected and applied intensity levels.

36 Claims, 18 Drawing Sheets

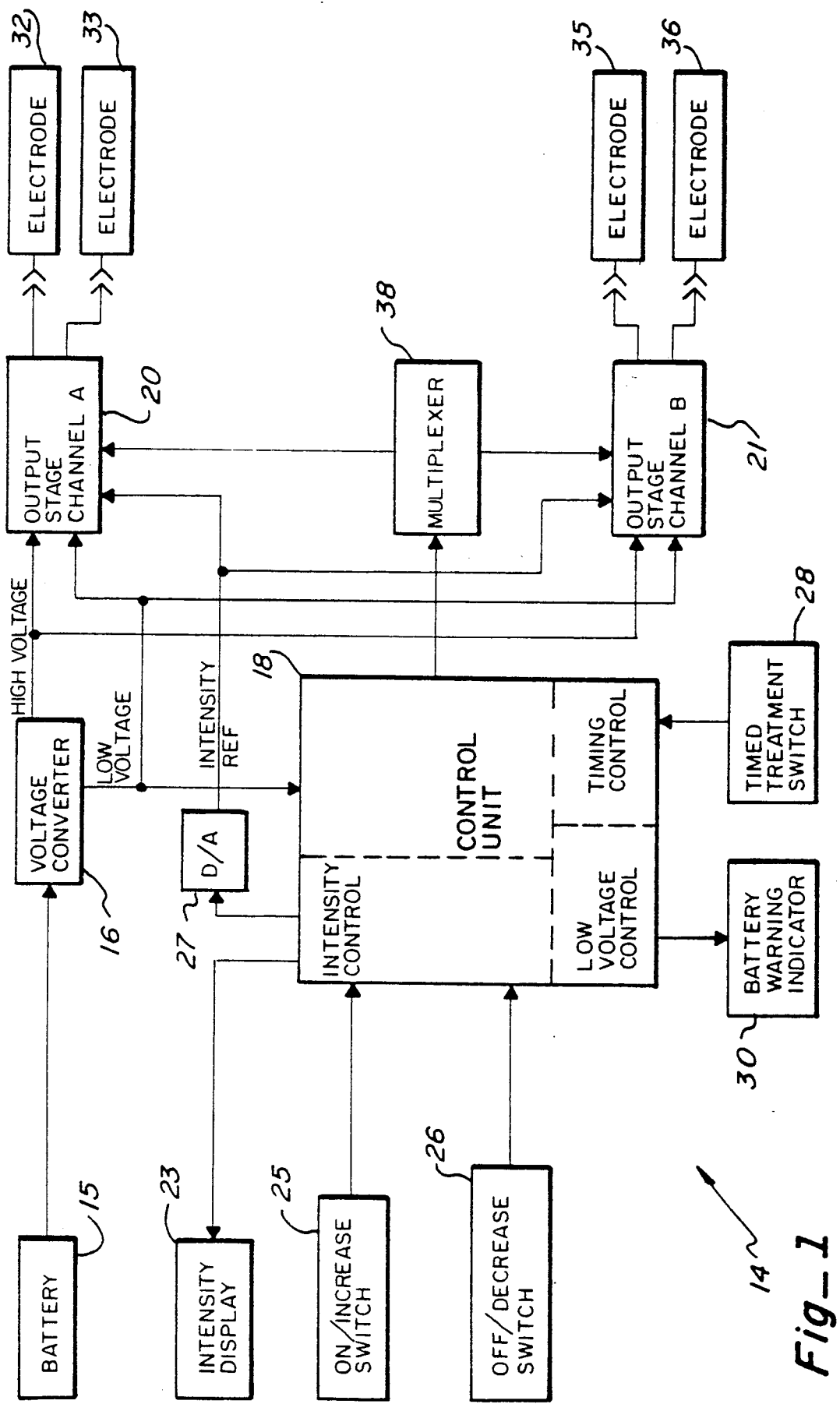
Fig_1

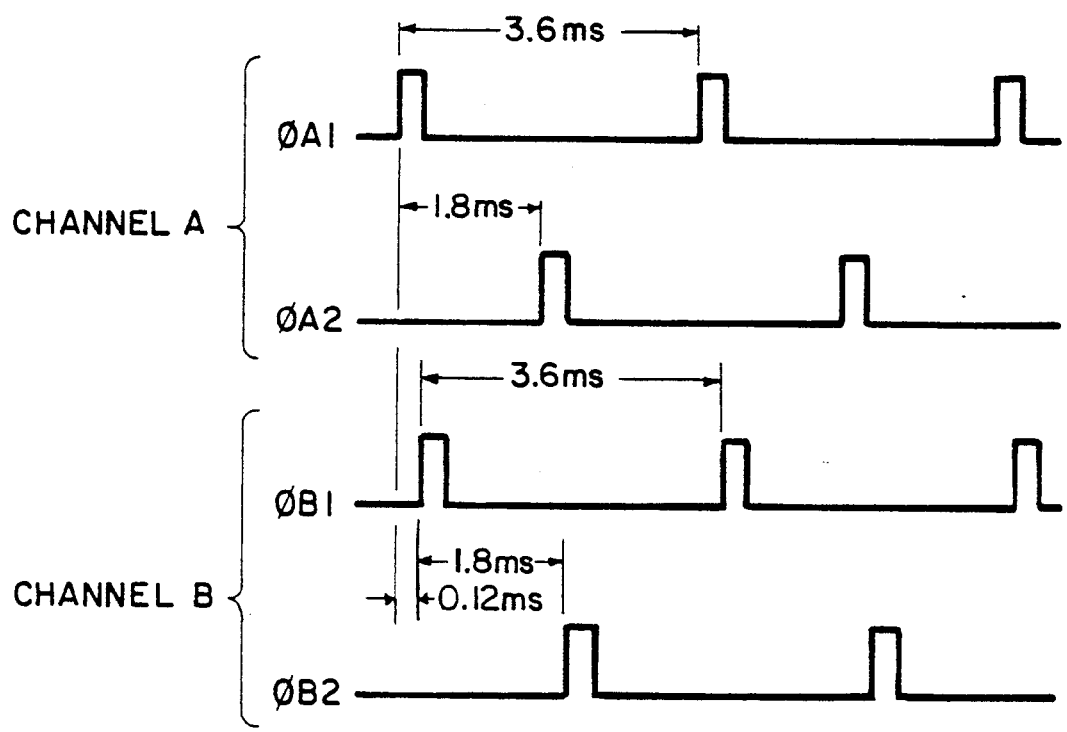
Fig_2
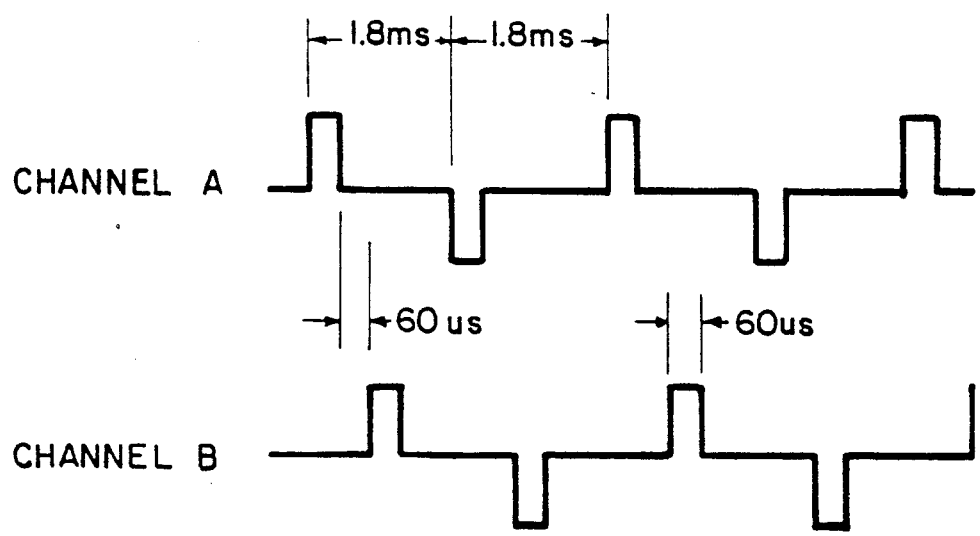
Fig_3

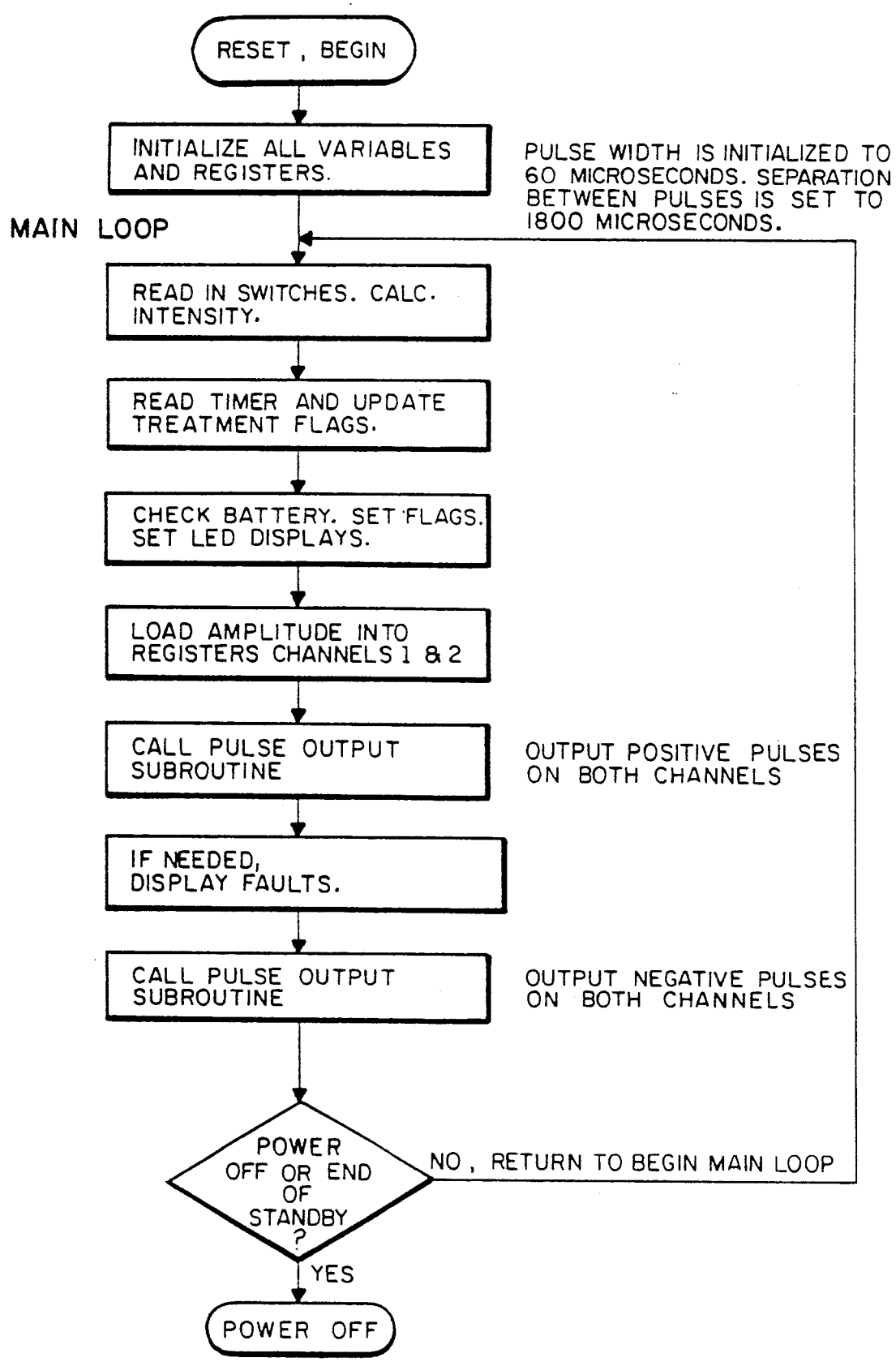
Fig_4A

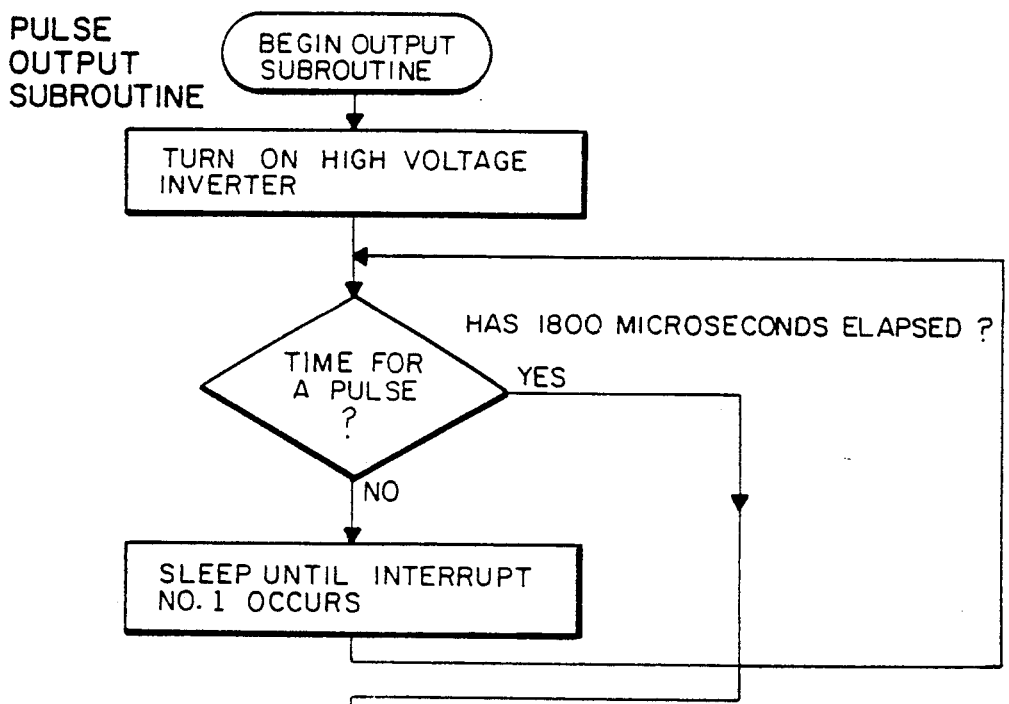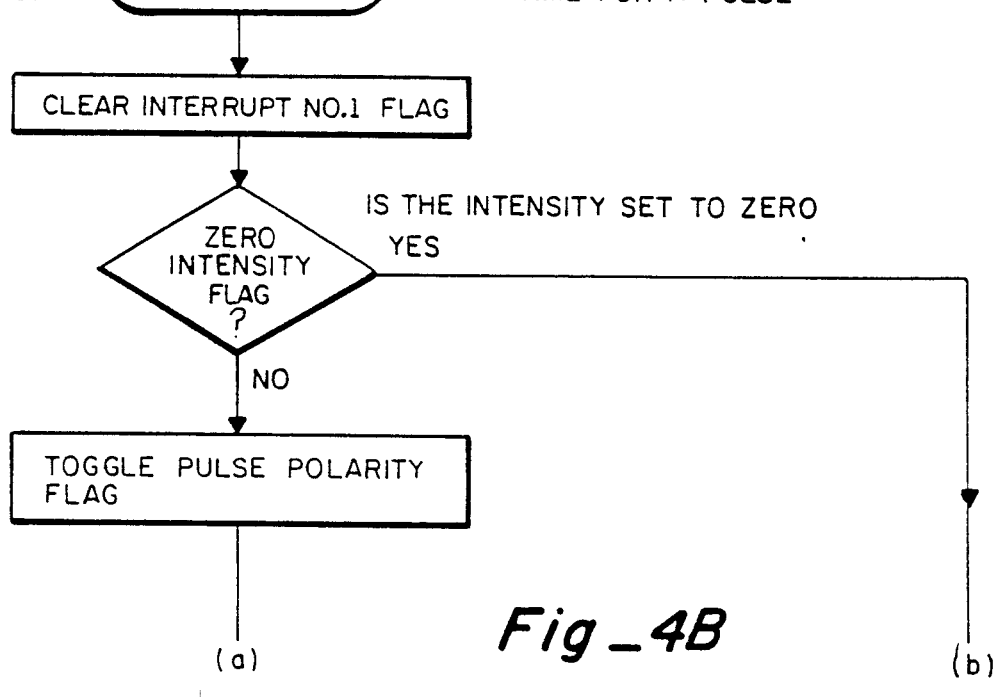
Fig_4B

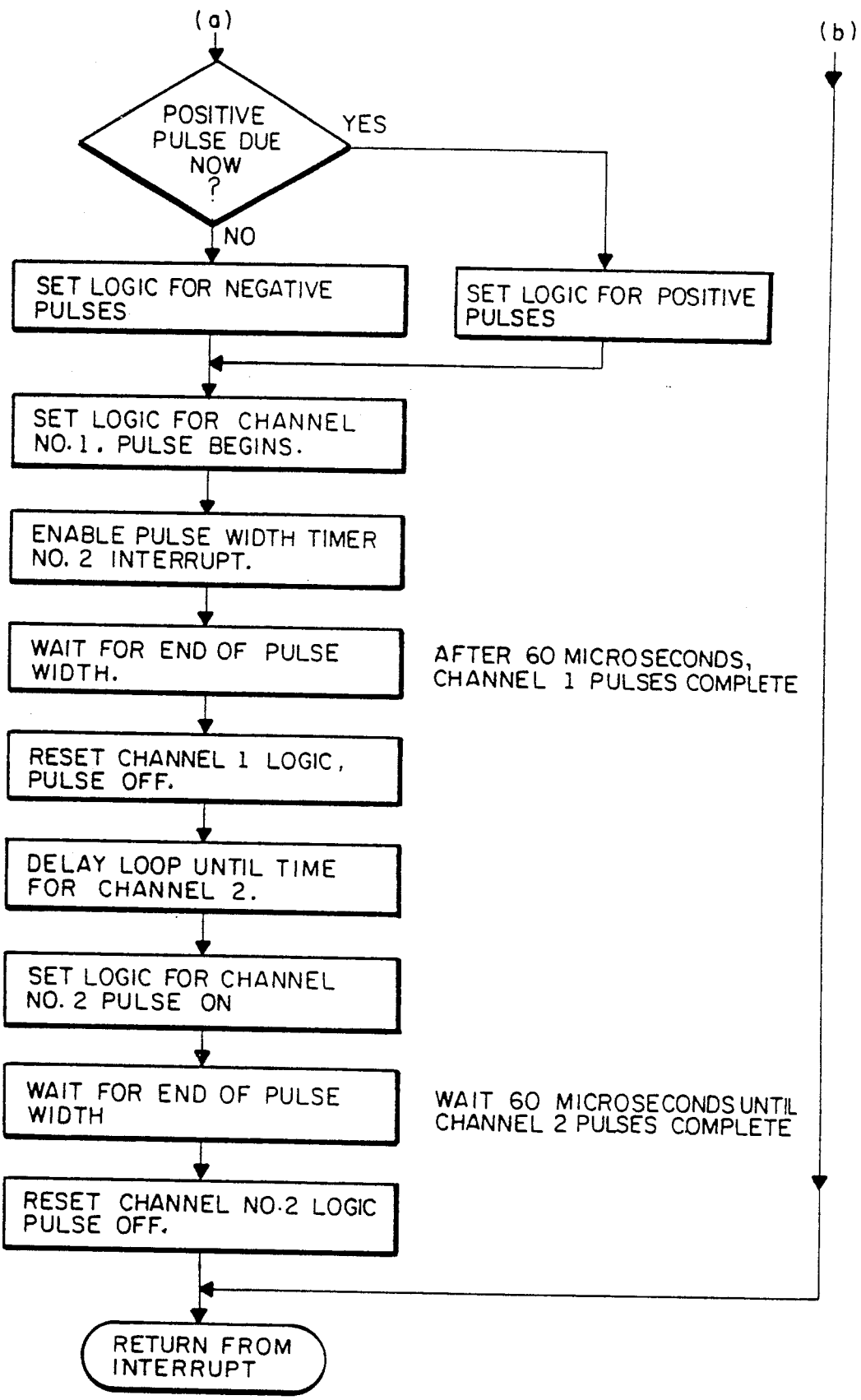
Fig_4C

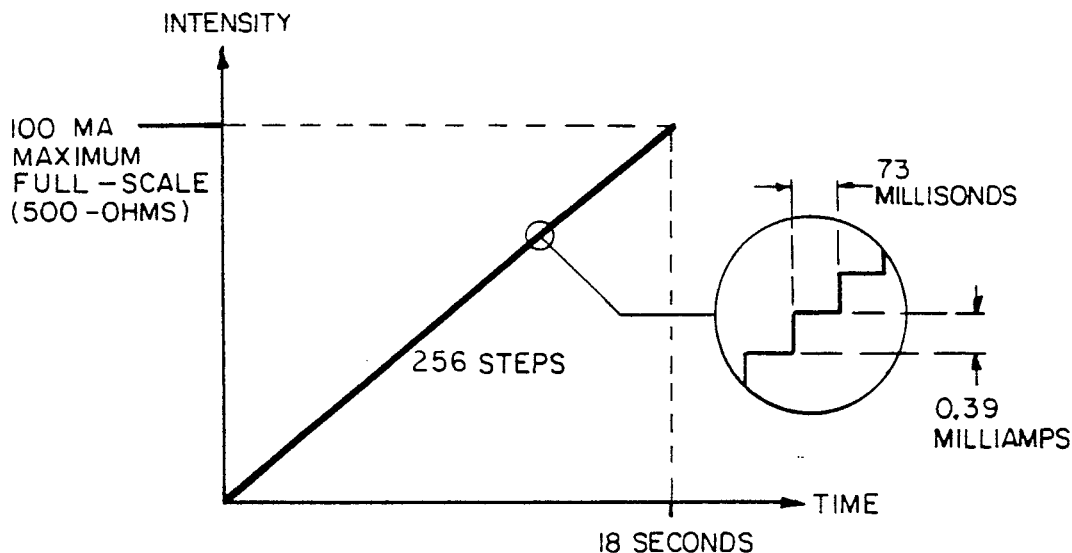
Fig_5
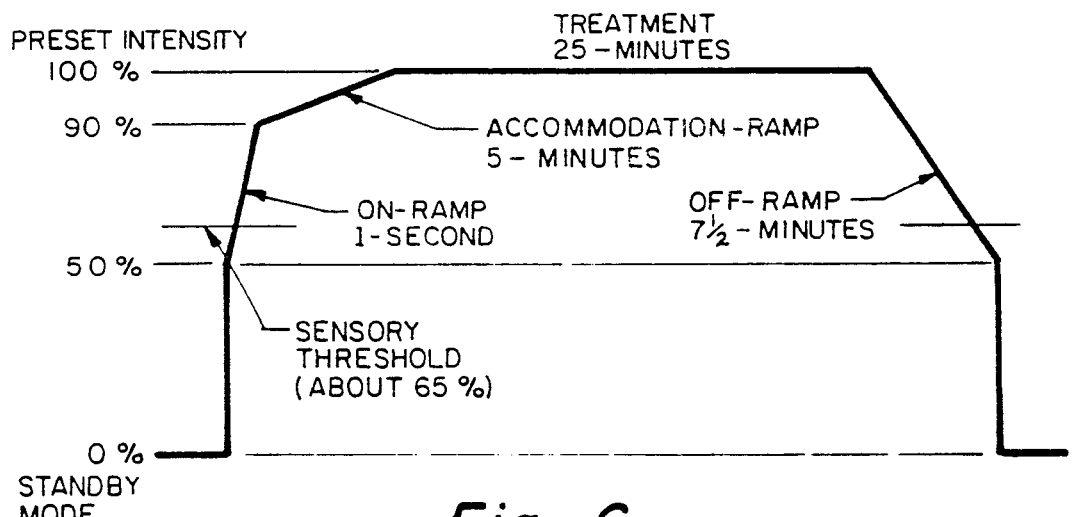
Fig_6
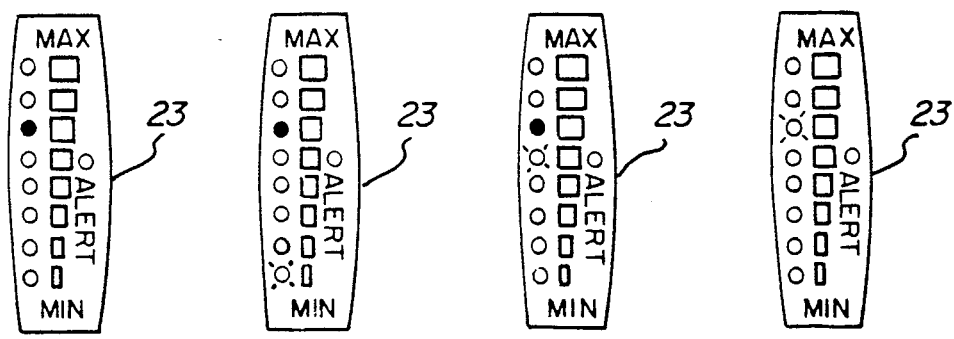
Fig_7A  Fig_7B  Fig_7C  Fig_7D

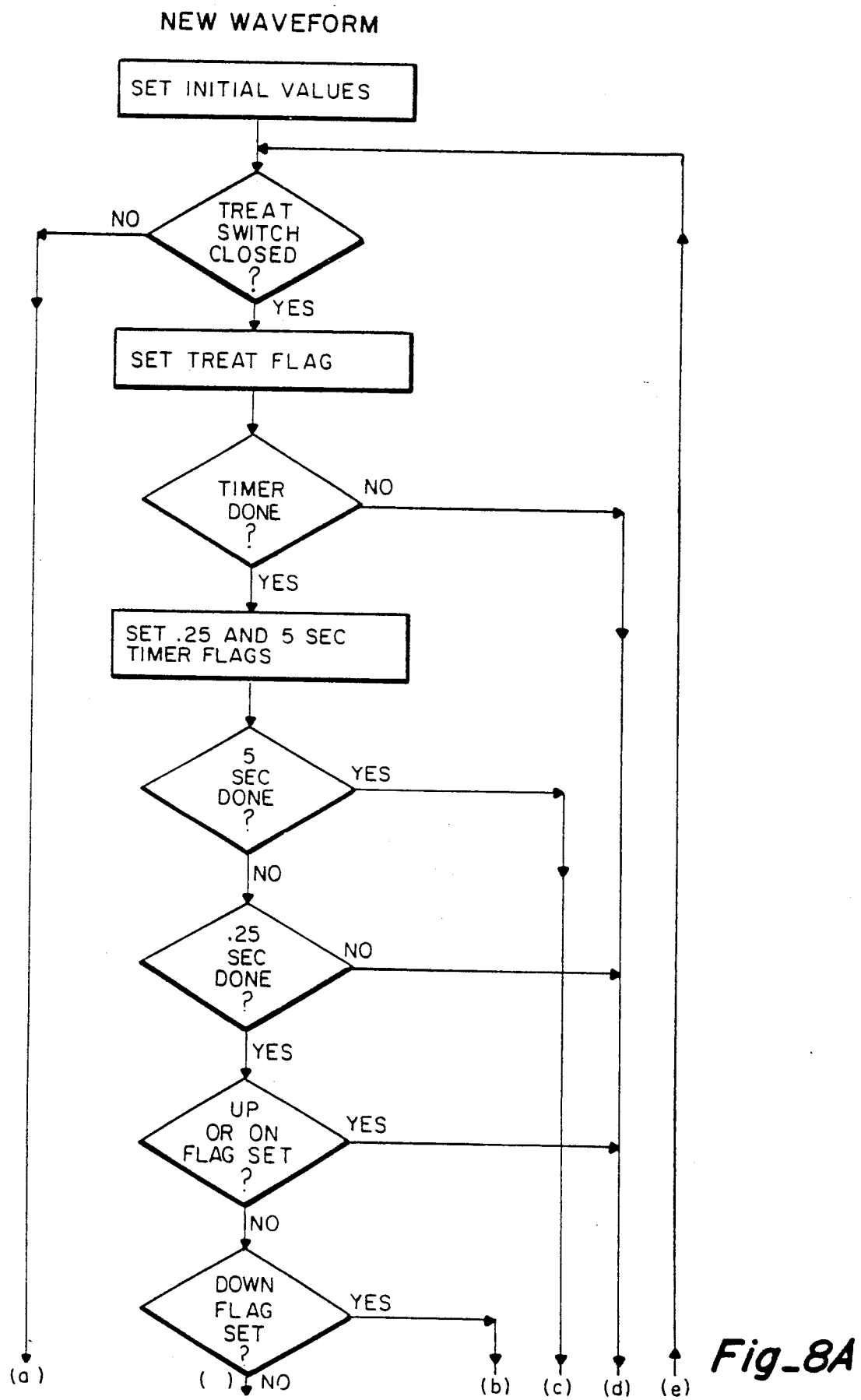
Fig_8A

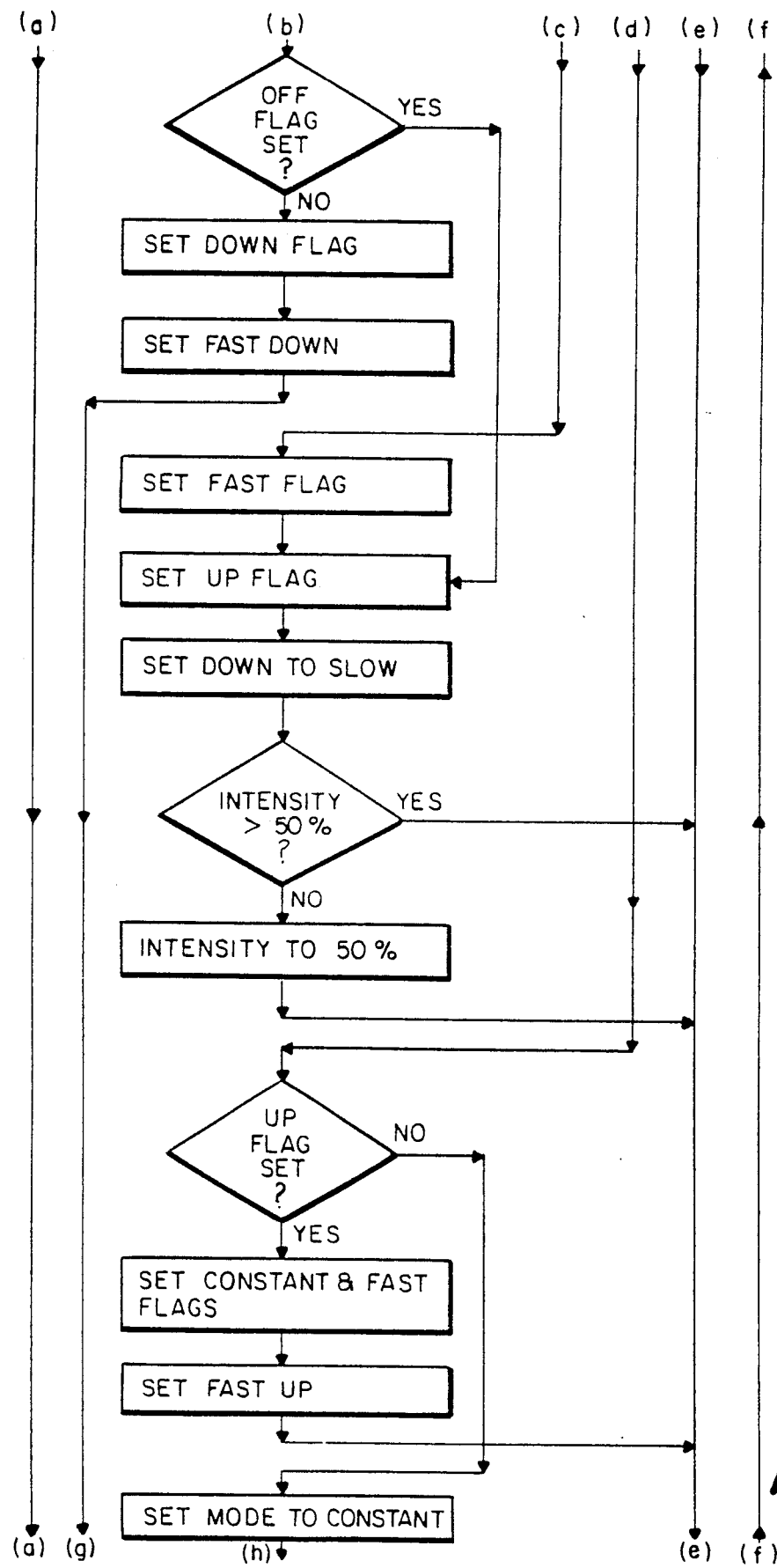
Fig_8B

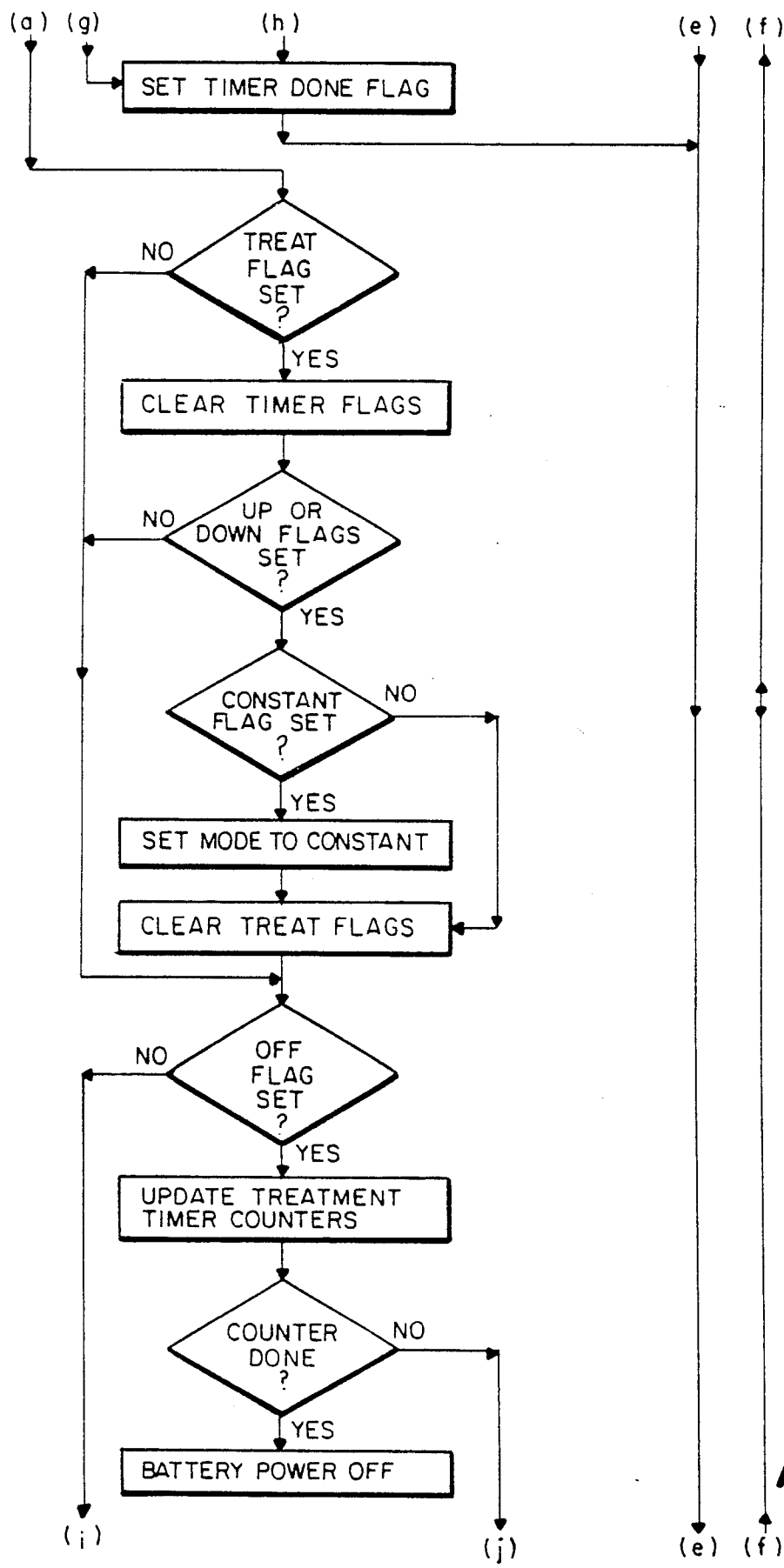
Fig_8C

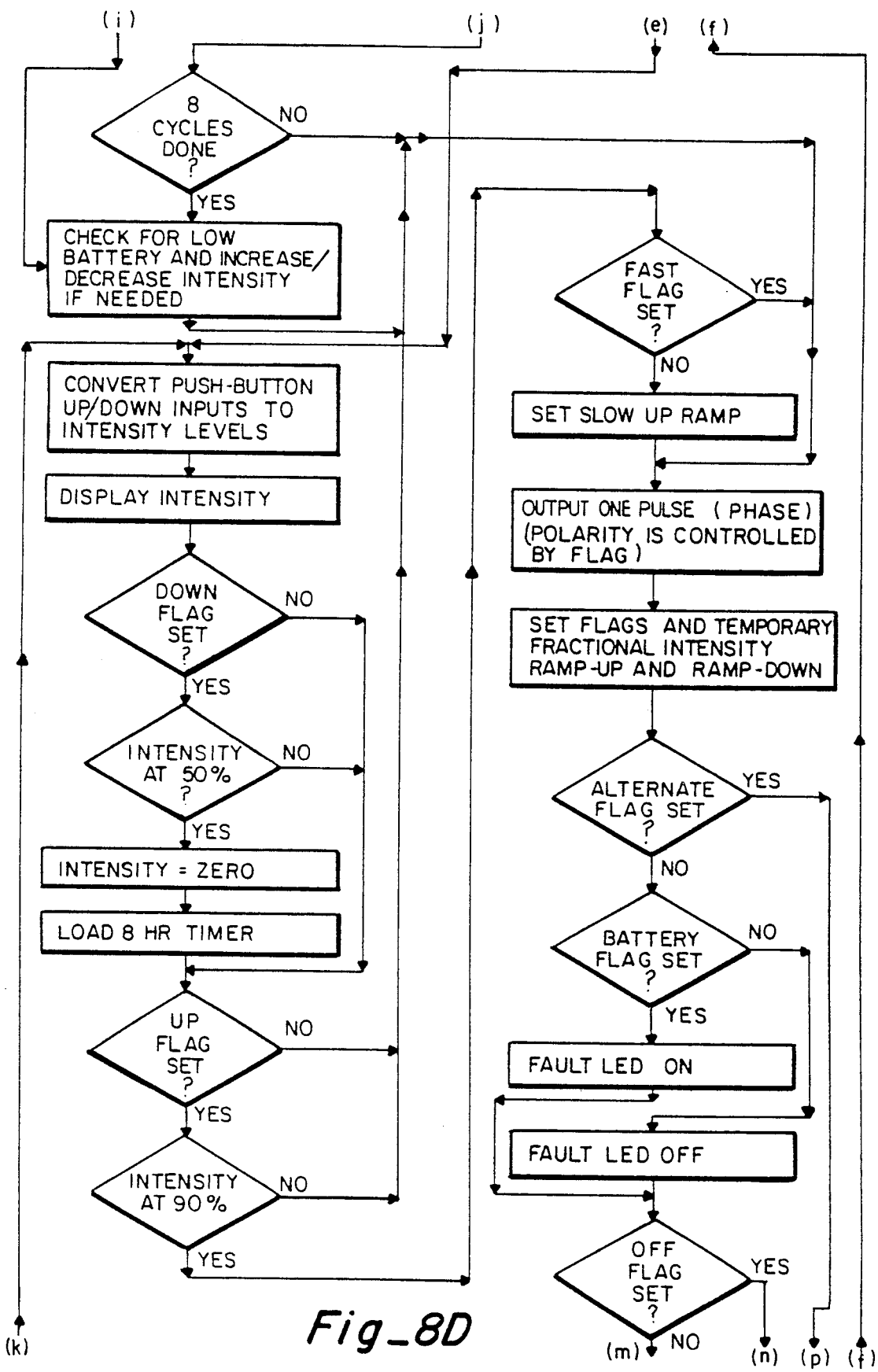
Fig_8D

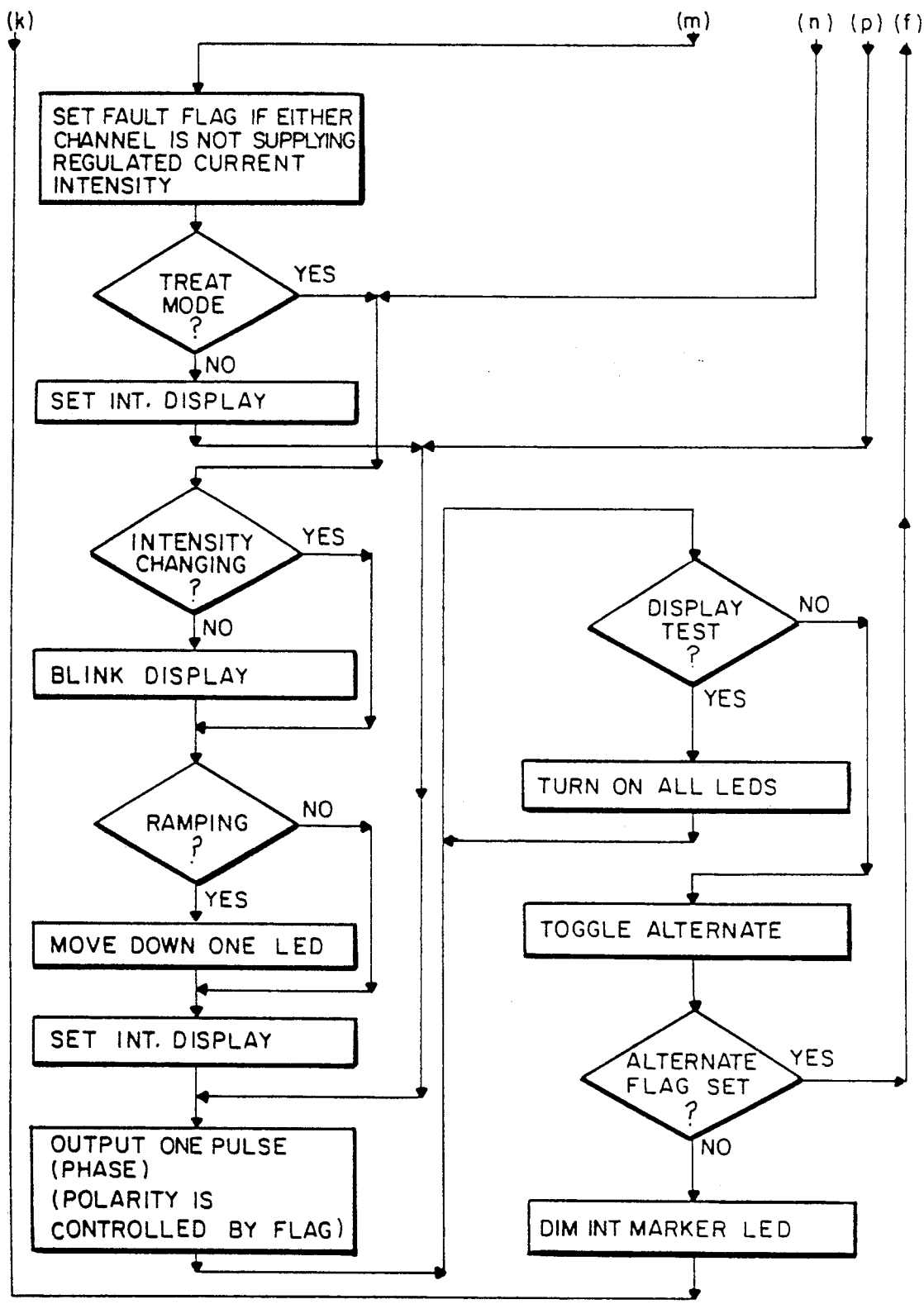
Fig_8E

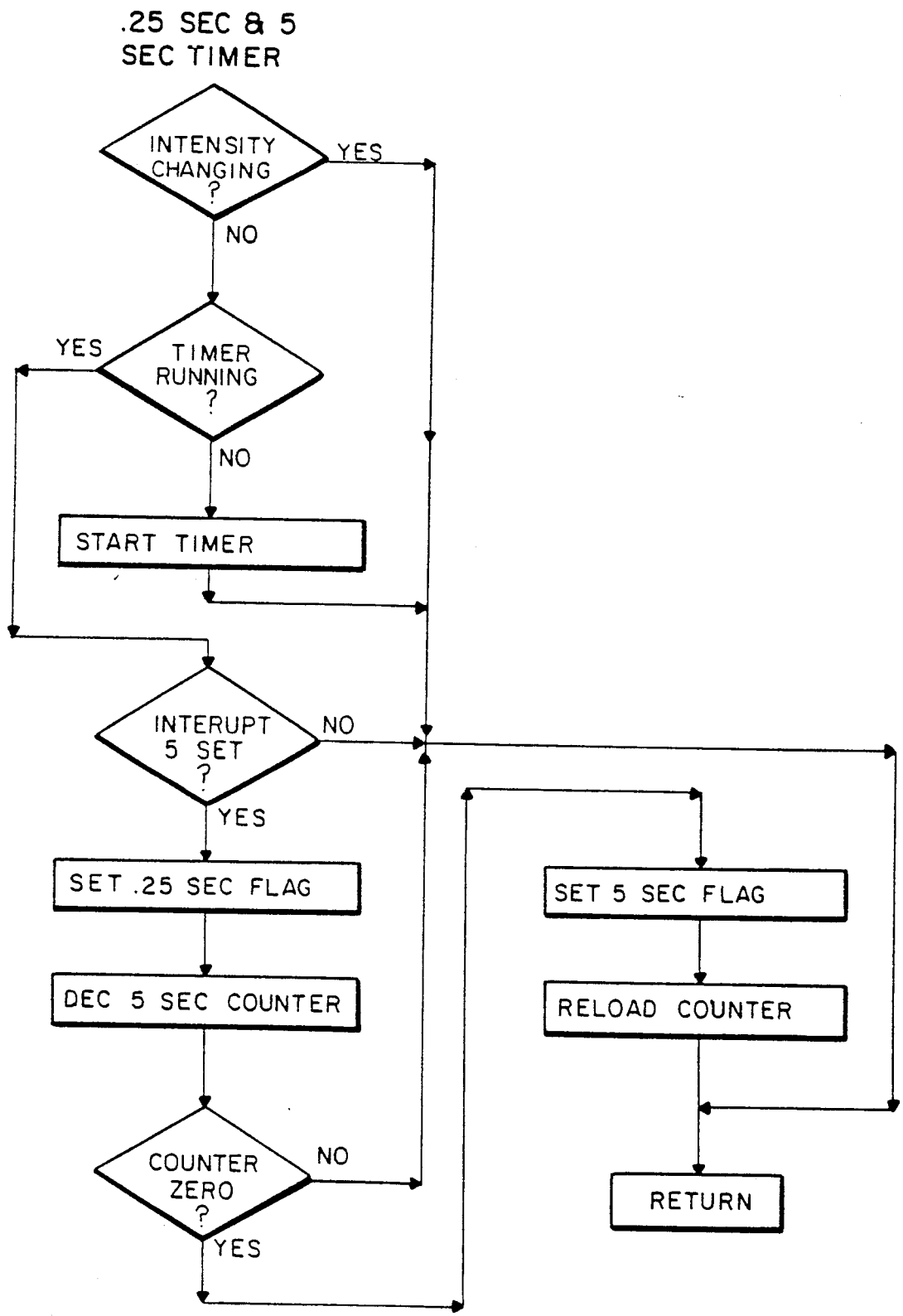
Fig_8F

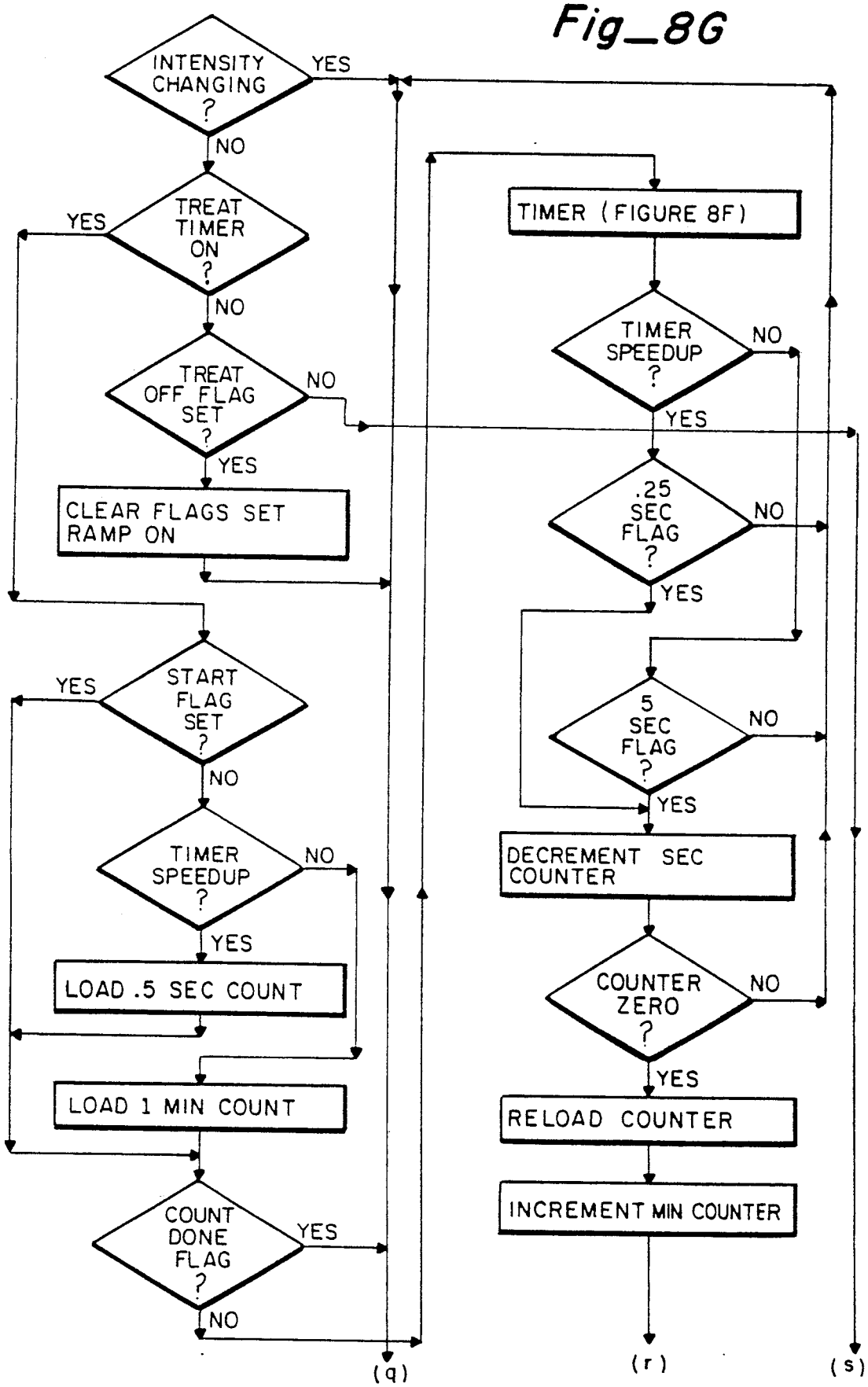
Fig_8G

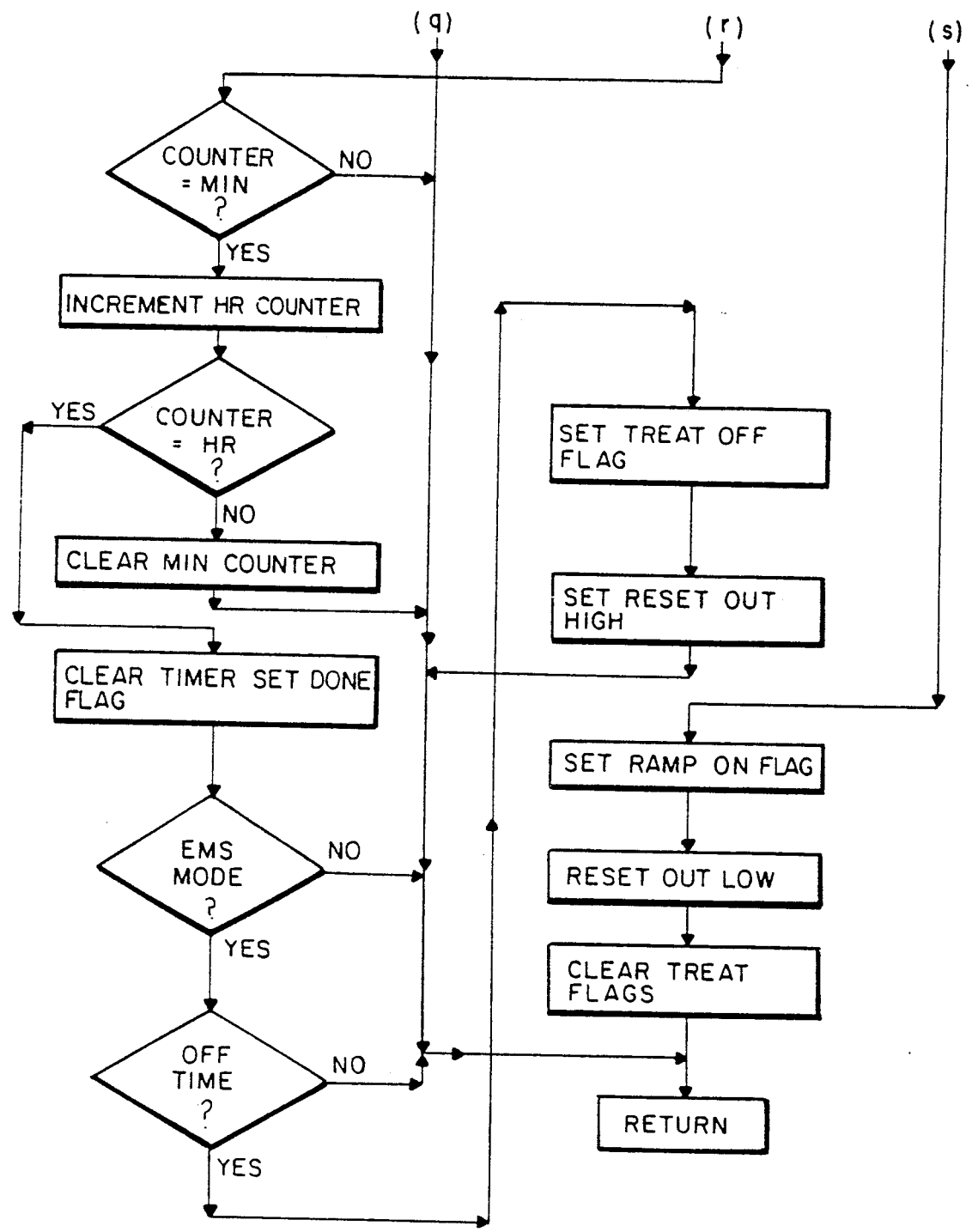
Fig_8H

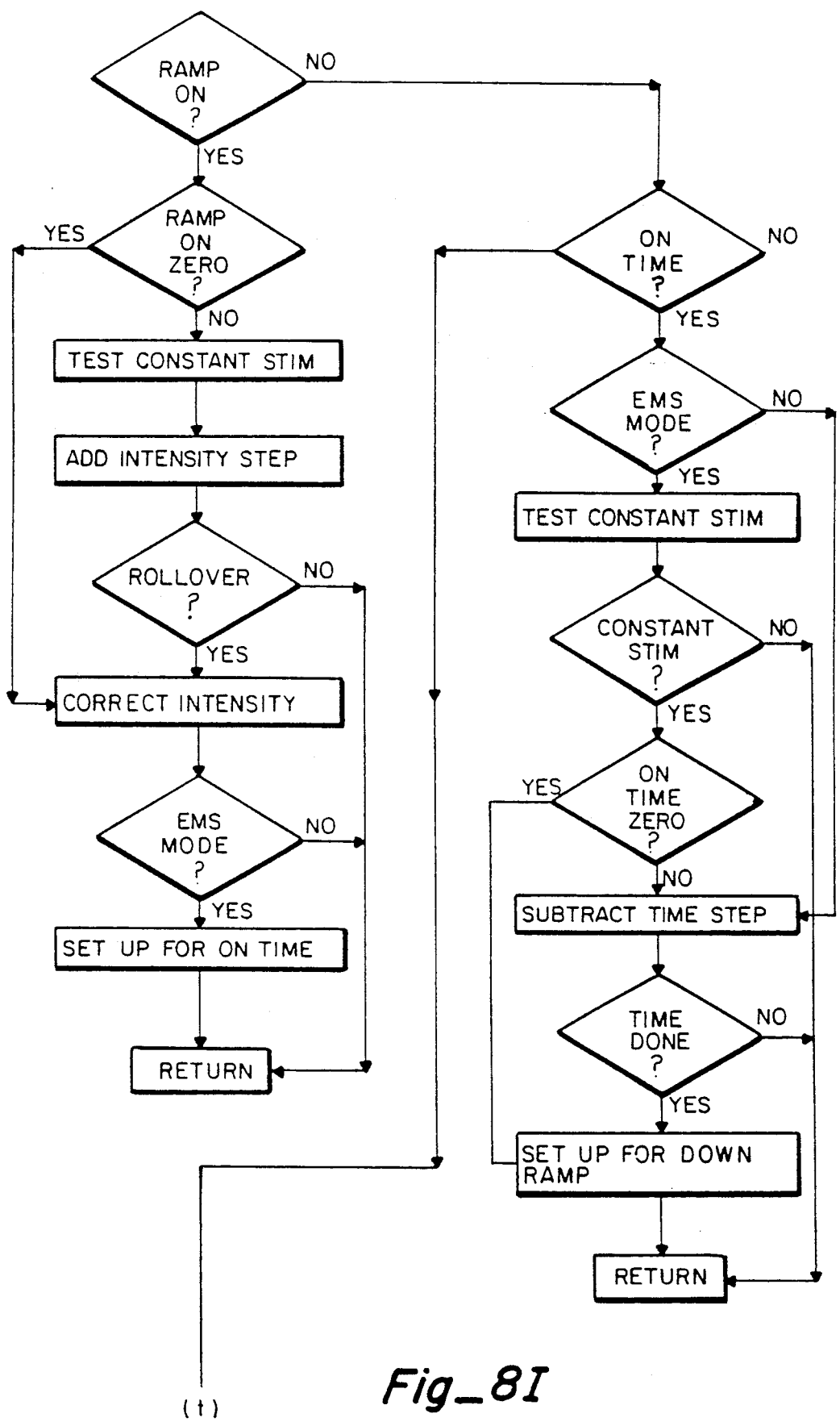
Fig_8I

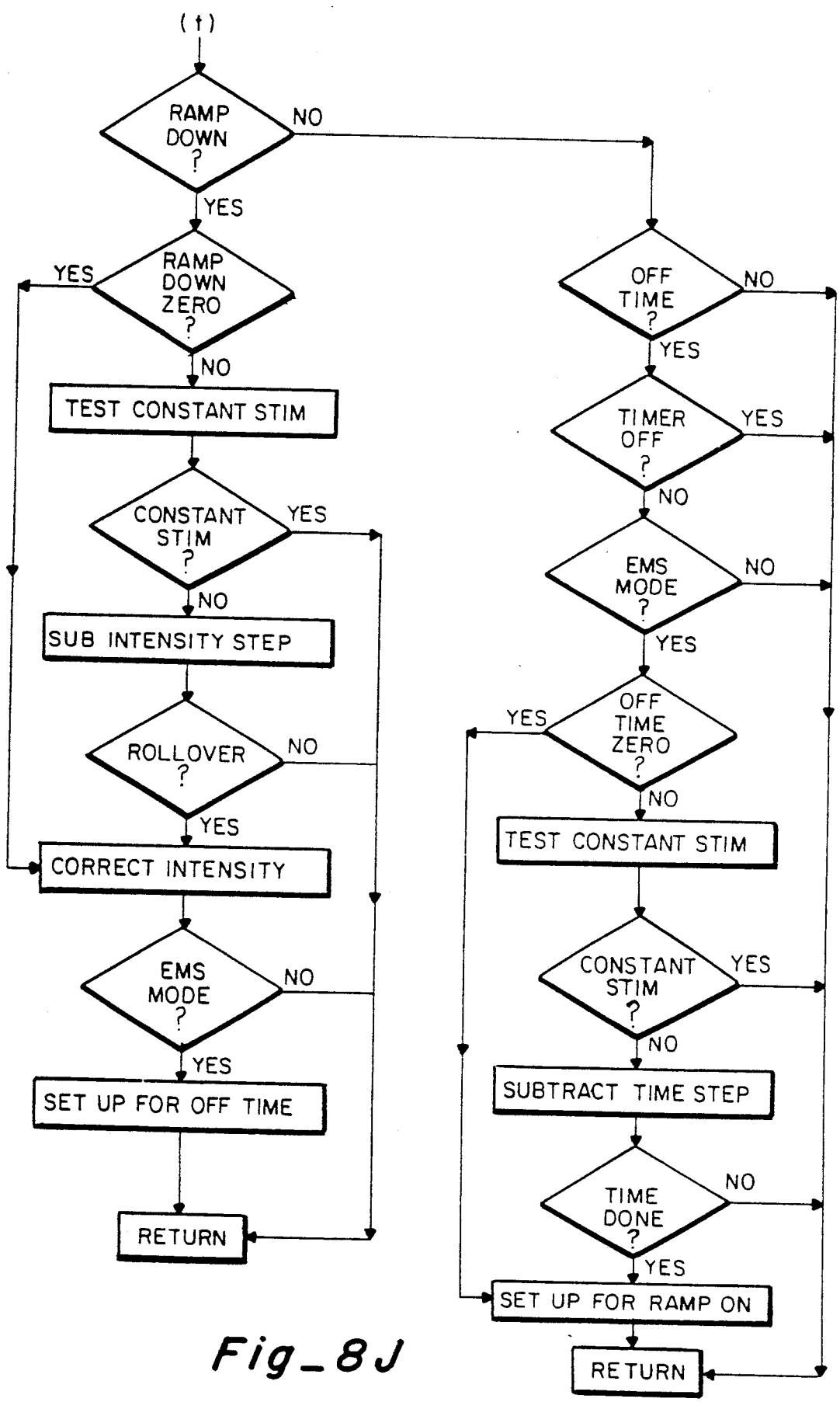
Fig_8J

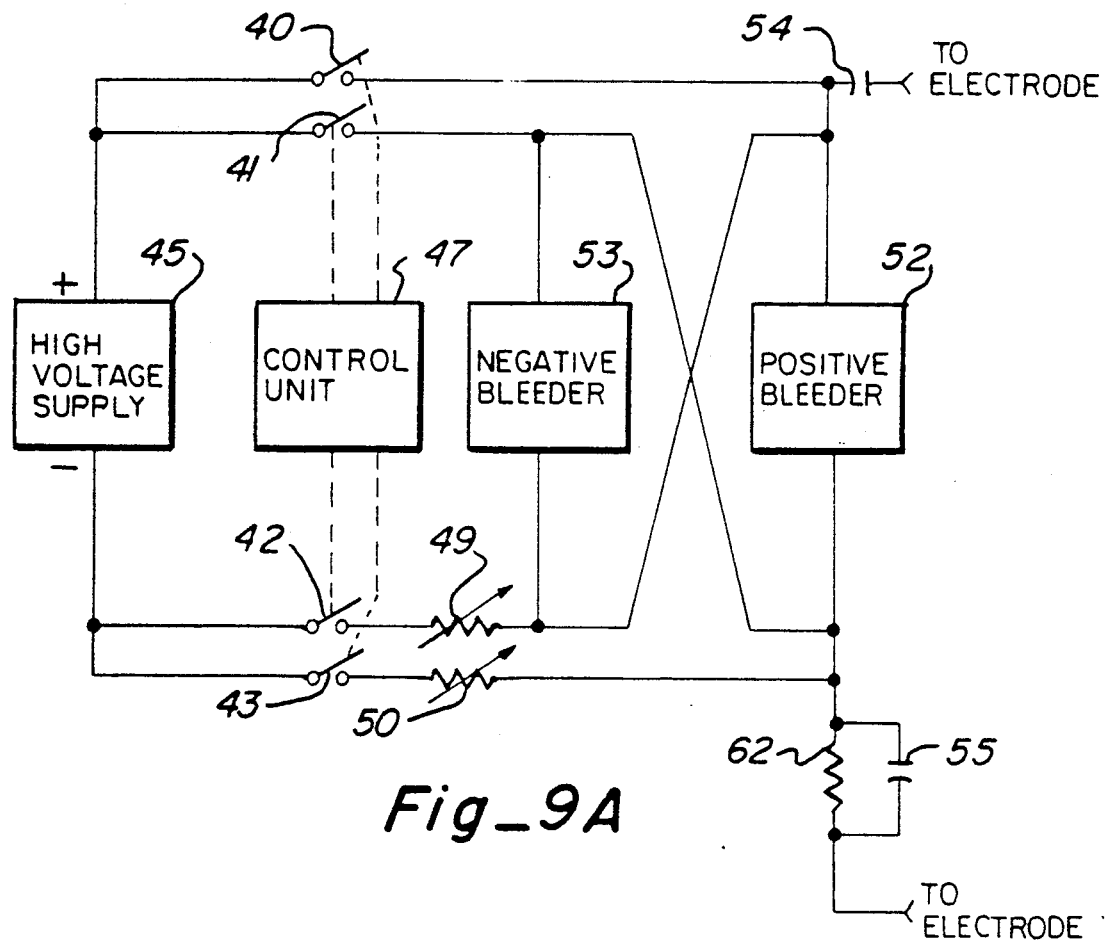
Fig_9A
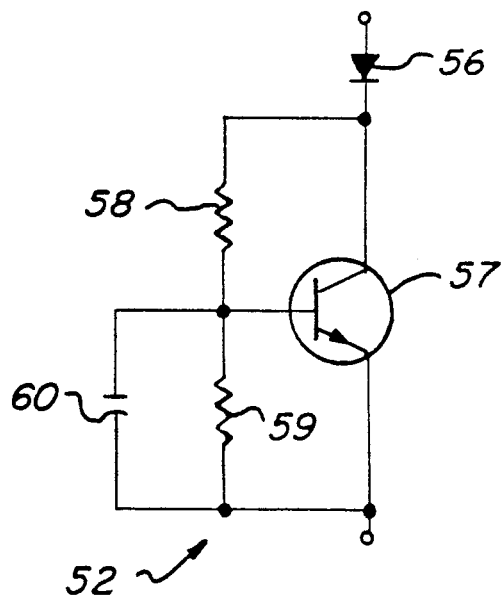
Fig_9B

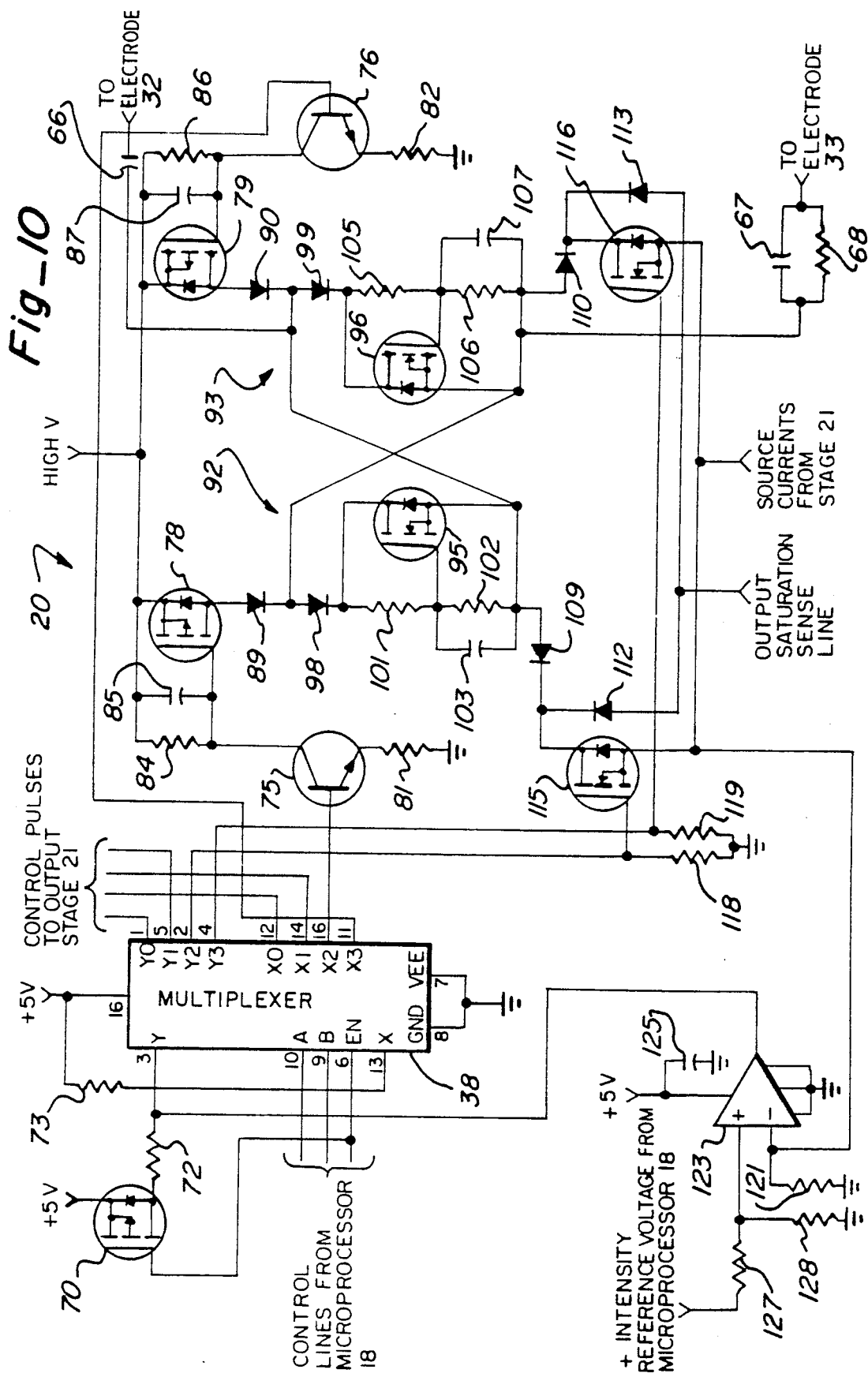

ELECTRONIC STIMULATING DEVICE HAVING TIMED TREATMENT OF VARYING INTENSITY AND METHOD THEREFOR

FIELD OF THE INVENTION

This invention relates to an electronic stimulating device, and, more particularly, relates to a device and method for effecting a timed treatment of varying intensity in an electronic stimulating device, such as a transcutaneous nerve stimulating (TENS) device.

BACKGROUND OF THE INVENTION

The use of electronic stimulating devices are now well known, and examples of such devices to suppress pain are also now well known (see, for example, in U.S. Pat. Nos. 4,014,347, 4,210,150 and 4,632,117).

It is also well known that such devices have heretofore commonly included externally actuable controls for varying intensity and/or other signal parameters (see, for example, U.S. Pat. No. 4,014,347).

More recently, it has been found that biphasic pulses can be used to good advantage in connection with electronic stimulating devices, and examples of devices generating biphasic pulses are shown, for example, in U.S. Pat. Nos. 2,375,575 3,946,745, 4,237,899 and 4,256,116.

Still more recently, it has been found that specific groupings of biphasic pulses can be used to increase the activity of selected nerve fibers (see U.S. Pat. No. 4,640,286). It has also been found that specific groupings of biphasic pulses can be used to good advantage with plural equally active electrodes (see U.S. Pat. No. 4,803,988), and, more particularly, with symmetrical biphasic pulses applied through equally active electrodes to one or more channels (see U.S. Pat. No. 4,813,418).

Transcutaneous nerve stimulating devices providing dual channel isolation and including capacitively coupled outputs have also heretofore been suggested for use with monopolar-type stimulation (see, for example, U.S. Pat. No. 4,632,117 wherein a high voltage power supply is connected to the electrodes by transistor switches controlled by control pulses provided thereto by a pulse generator, with the power supply being isolated from the user by a capacitor/diode arrangement so that the device cannot directly deliver any net DC charge to the user, and with a bleeder resistor that discharges the output capacitor during the intervals between the pulses).

Microprocessor controlled transcutaneous nerve stimulating devices have also been heretofore suggested for use with transformer coupled transcutaneous nerve stimulating devices producing a biphasic pulse output (see, for example, U.S. Pat. No. 4,640,286).

Thus, while electronic stimulating devices, including transcutaneous nerve stimulating devices have been heretofore suggested, and while such devices have heretofore been extensively modified, additional improvements can still be utilized to good advantage.

SUMMARY OF THE INVENTION

This invention provides an improved electronic stimulating device, such as a transcutaneous nerve stimulating (TENS) device, that includes a timed treatment of varying intensity, together with a method for effecting the timed, varying intensity treatment, and a display of both selected and applied intensities.

The device includes a control unit, preferably a microprocessor control unit, for generating control pulses that are provided to one or more output stages, or channels, along with high voltage so that each output stage generates biphasic output pulses, which pulses are controllable as to intensity and are coupled from each output stage for application to a user through an electrode pair non-invasively positioned at the skin of the user, with a display of selected and applied intensities also being provided.

It is therefore an object of this invention to provide an improved electronic stimulating device providing a timed treatment of varying intensity.

It is another object of this invention to provide an improved transcutaneous nerve stimulating device as the electronic stimulating device providing a timed treatment of varying intensity.

It is still another object of this invention to provide an improved electronic stimulating device having a display of selected and applied stimulation intensities.

It is still another object of this invention to provide an improved electronic stimulating device that is microprocessor controlled.

It is still another object of this invention to provide a device and method for effecting a timed treatment by varying stimulation intensity.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a block diagram illustrating an electronic stimulating device, which device is illustrated as a transcutaneous nerve stimulating device, and which device includes provision for timed treatment of varying intensity of stimulation;

FIG. 2 illustrates typical control pulses provided by the microprocessor to control generation of biphasic output pulses at the dual output stages as shown in FIG. 1;

FIG. 3 illustrates typical biphasic pulse outputs coupled from the dual output stages as shown in FIG. 1;

FIGS. 4A through 4C, taken together, form a flow chart for generation of control pulses using a microprocessor as the control unit;

FIG. 5 is an illustration of intensity variation by steps as effected by the control unit;

FIG. 6 is an illustration of the algorithm utilized by the microprocessor control unit during a programmed treatment mode;

FIGS. 7A through 7D illustrate the intensity display and operation thereof;

FIGS. 8A through 8J, taken together, form a flow chart for programmed timing by the microprocessor control unit according to the algorithm as set forth in FIG. 6;

FIG. 9A is a simplified illustration of a capacitively coupled output stage providing a biphasic pulse output;

FIG. 9B is a schematic diagram illustrating the bleeder circuitry shown in block form in FIG. 9A; and FIG. 10 is a schematic diagram of a capacitively coupled output stage for effecting a biphasic pulse output at varying intensities.

DESCRIPTION OF THE INVENTION

An electronic stimulating device, and, more particularly, a transcutaneous nerve stimulating device 14, is shown by the block diagram of FIG. 1. As shown, battery 15 is utilized as the sole power source to power device 14. Battery 15, preferably a 9 volt battery, is connected with conventional voltage converter, or inverter, 16, and converter 16 supplies a low voltage DC output, preferably 5 volts, to microprocessor control unit 18, as well as to output stages, or channels, 20 and 21. In addition, converter 16 also supplies a high voltage DC output, preferably 100 volts maximum, to output stages 20 and 21.

Microprocessor control unit 18 has an intensity display 23 connected therewith, with the intensity being varied by intensity on/increase switch 25 and intensity off/decrease switch 26, both of which are externally actuatable. As also indicated, an intensity reference (the level of which is selected using intensity switches 25 and 26 in conjunction with the intensity control provided by control unit 18) is supplied by microprocessor control unit 18, converted to analog form in digital-to-analog (D/A) converter 27, and then coupled to output stages 20 and 21.

Microprocessor control unit 18 also provides a timing control (for use during the programmed treatment mode of operation of the device) that is activated by timed treatment switch 28. In addition, microprocessor control unit 18 can include a low voltage control with detected low battery voltage being indicated at battery warning indicator 30.

Output stage 20 (channel A, or 1, as also referred to herein) is connectable with electrodes 32 and 33, providing a first electrode pair, and output stage 21 (channel B, or 2, as also referred to herein) is connectable with electrodes 35 and 36, forming a second electrode pair.

Microprocessor control unit 18 generates control pulses, as typically shown in FIG. 2, with the control pulses designated for channel A being coupled through multiplexer 38 to output stage 20, and with the control pulses designated for channel B being coupled through multiplexer 38 to output stage 21, to control generation of the biphasic pulse outputs at each output stage, or channel, as typically shown in FIG. 3.

A more detailed explanation of the control pulses, as well as the biphasic pulse output to be provided, is set forth U.S. Pat. No. 4,813,418, which is hereby incorporated herein by reference. A flow chart for pulse generation using a microprocessor is shown in FIGS. 4A through 4C. While microprocessor control unit 18 is now preferred, apparatus for producing control pulses, as shown and described in U.S. Pat. No. 4,813,418 could also be utilized as the control unit.

The device can operate in either of two modes, namely a continuous stimulation mode or a programmed treatment mode. In either mode, a biphasic pulse output is provided.

For operation during a continuous stimulation mode, the selected level of stimulation is the stimulation provided by the biphasic pulse output, to the extent that the device is capable of producing a biphasic pulse output at the level selected. Control unit 18, in conjunction with digital-to-analog converter 27, provides intensity control to the output stage units 20 and 21, preferably by causing a stepped output as indicated in FIG. 6.

For operation during the programmed treatment mode, it has been found to be preferable to provide different multi-step intensity level variations for both turn-on and turn-off. An algorithm for establishing operation during a programmed treatment is shown in FIG. 6.

The algorithm, as set forth in FIG. 6, has been established keeping in mind the following: when pain occurs the user wants prompt relief and it is therefore necessary, or at least advisable, that the intensity be increased rapidly so that the user quickly feels that stimulation is being applied (in the algorithm as shown in FIG. 6, the intensity is caused to go up immediately to a 50% level of selected full intensity, which level is below the sensory threshold of the user which is assumed to be about 65% of the maximum comfortable level selected by the user); although stimulation is to be felt immediately, such stimulation should not reach the sensory threshold level so abruptly that it is startling (in the algorithm as set forth in FIG. 6, the intensity is therefore increased from 50% of selected full intensity up to 90% of selected full intensity during a one second interval which has been found to be just sufficient to prevent the user from being startled); it has also been found that, after the intensity has been selected, it is normally not necessary to readjust the intensity control during treatment so long as the intensity level has been set as high as possible without causing discomfort, the level that fits this perception, however, changes during the first five minutes of treatment as the nerves accommodate to the applied stimulation (in the algorithm as set forth in FIG. 6, the sensation is maintained by increasing the intensity slowly from 90% of selected full intensity to the selected full intensity over a five minute interval); and, while the exact overall treatment time is not critical, it should preferably range between about 10 minutes to about 60 minutes (in the algorithm as set forth in FIG. 6, a treatment time of about one-half hour is utilized).

Accordingly, in this device, after a programmed treatment has been initiated, the intensity is allowed to be increased quite rapidly, or abruptly (i.e., substantially instantaneously), to 50% of the selected full intensity level at commencement of treatment (with treatment being commenced by depressing timed treatment switch 28), and the intensity is then allowed to increase to 90% of the selected full intensity level during the next one second (the sensory threshold occurs during this one second on-ramp interval as indicated in FIG. 6). After reaching the 90% of selected full intensity level, the intensity is then increased slowly during an accommodating-ramp for the next five minutes to the selected full intensity level, and this full intensity is then maintained for a period of 25 minutes, after which the intensity is slowly decreased during an off-ramp over a period of 7 ½ minutes to the 50% of selected full intensity level. The intensity level is then quite rapidly, or abruptly, reduced (i.e., substantially instantaneously) to zero.

Intensity display 23 is utilized to indicate, by a continuous visual indication (by, for example, energizing a red light emitting diode (LED)), the intensity selected. As illustrated in FIG. 7A, the display utilized is an array of visual indicators (preferably made up of a plurality of LEDs (while 8 LEDs are illustrated in FIG. 7, 16 LEDs are preferably utilized) arranged in a row to form a bar graph). The selected level can be increased by actuation of on/increase switch 25 or decreased by actuation of off/decrease switch 26 and this causes the visual indication to be moved (by successively energizing and de-energizing each succeeding LED in the row of LEDs) to indicate the selected intensity (i.e., if the increase switch is actuated, the visual indication will be moved toward the maximum intensity level as indicated on intensity display 23, as shown in FIG. 7A, while if the decrease switch is actuated, the visual indication will be moved toward the minimum intensity level as indicated on intensity display 23, as also shown in FIG. 7A).

For the continuous stimulation mode, the delivered intensity will be the selected intensity so long as the device is capable of delivering the intensity selected, and hence only a continuous visual indication, such as illustrated in FIG. 7A, is utilized.

For the programmed treatment mode, timed treatment switch 28 is briefly depressed to select the programmed treatment mode, and such selection is indicated at the intensity display by a second visual indication that is repeatedly energized and de-energized to establish a blinking visual indication, as illustrated in FIGS. 7B through 7D. This indication, at minimum (zero) intensity, as indicated in FIG. 7B, is a standby condition with no stimulation being provided.

To initiate a programmed treatment, timed treatment switch 28 is again briefly depressed to start a programmed treatment cycle. The blinking visual indication will move (by repeatedly energizing and then de-energizing each succeeding LED in the row of LEDs) toward the constant visual indicator, as indicated by a comparison of FIGS. 7B and 7C, to illustrate to the user that the level of intensity of the treatment is increasing (i.e., it is following the algorithm as set forth in FIG. 6). When the level of intensity reaches the selected level, the blinking visual indication will merge with the steady indication and only a blinking indication, as indicated in FIG. 7D, will be observed during treatment at the selected intensity.

After treatment at the selected intensity, the blinking indicator will be moved toward the minimum level and the continuous, or steady, indicator will also then again be displayed (in the same manner as indicated in FIG. 7C), and after treatment has been terminated, the blinking indicator will again be at minimum level (in the same manner as indicated in FIG. 7B). At this time, the device is again in the standby condition, and will remain in this condition until a new treatment is initiated, or the device is turned off either manually or automatically.

In the standby condition, the preset maximum comfortable level is preserved in memory. The timer algorithm program allows the standby condition to persist for eight hours. After eight hours, if no new treatment has been initiated, the device is automatically shut off to save battery energy.

During programmed timing, stimulation is applied for a fixed time interval to prevent overtreatment. The slow turn-on compensates for nerve accommodation, and the slow turn-off terminates treatment without distracting the patient. As brought out above, programmed timing during the programmed treatment mode follows the algorithm set forth in FIG. 6, and programmed timing according to this algorithm is carried out by microprocessor control unit 18, as illustrated by the flow charts of FIGS. 8A through 8J.

The use of the programmed treatment is felt to give the user a feeling of control, automatically limits the treatment to a predetermined time interval to normally avoid muscle soreness often experienced by a user applying stimulation for too long a period, facilitates use of the device intermittently to increase the magnitude of sensation when a new programmed treatment is initiated, allows the strongest comfortable stimulation intensity once set to be repeated with no further need to adjust the intensity, compensates for the accommodation that normally occurs during the first five minutes of treatment, prolongs battery life, and provides the tingling sensation that at least some users prefer to provide confidence to the user that the device is indeed working.

The biphasic pulse output supplied to a user provides a pronounced paresthesia that persists for many minutes after treatment. This tingling sensation and numbness has been found not to be as pronounced as when intensity is set to the maximum strong comfortable level, but has been found by users to be obvious enough that at least some such users have stated that they cannot tell when the treatment has ended because the tingling persists long after terminated of the application of the pulses.

If the stimulation has relieved the user's pain, the user will normally become engrossed in activities and should not be aware of the device use or pain. In contrast, if a user attempts a one-half hour treatment that is not automatically timed, when the treatment time is completed, the user will often forget to turn off the device, and this will drain the battery and could lead to muscle soreness. For this reason, use of the device in the programmed treatment mode further enhances both use of the device and effectiveness of treatment.

A biphasic output stage requires circuitry that enables generation of pulses having both positive and negative polarities. As indicated by the simplified schematic diagram of FIG. 9A, this can be accomplished using four transistor switches 40, 41, 42 and 43. Switches 40 and 41 are gate on/off transistors that connect high voltage supply 45 to an electrode pair (such as, for example, by providing high voltage from converter 16 to electrodes 32 and 33, as indicated in FIG. 1) at different times. The transistors are turned-on by control pulses supplied thereto from control pulse generator 47 (which pulses can be generated, for example by microprocessor control unit 18, as indicated in FIG. 1) with the control pulses provided being as indicated, for example, in FIG. 2 (it being realized that the pulse spacing between channels could be varied, as, for example, utilizing 180 ms between occurrences of like pulses on different channels as is now preferred for some TENS devices now provided).

Switches 42 and 43 functionally include variable resistance represented in FIG. 9A as variable resistors 49 and 50 connected in series therewith and these transistors serve both as switches and current level control variable resistors. When not turned on by a control pulse, the transistors are off and have infinite resistance. When a biphasic pulse output is produced (such as shown in FIG. 3, for example), conductance is determined by a voltage reference that sets the desired level of current for the pulses. Since variable-resistor/switch transistors 42 and 43 are connected to opposite electrodes, they cannot be combined and must be separate transistors that are turned on at different times by control pulses.

Positive and negative bleeder networks, or circuits, 52 and 53 discharge any voltage that may appear across output capacitors 54 and 55 (used to capacitively couple the output pulses from the device to the associated electrodes). If the two polarities of the output stage are perfectly balanced, the pulses generated can contain precisely the same charge and there would be no need for a bleeder circuits, but this, most often, does not occur.

Positive bleeder circuit 52 is shown in schematic form in FIG. 9B (negative bleeder circuit 53 is identical to positive bleeder circuit 52 and has not been specifically illustrated). As shown in FIG. 9B, positive bleeder circuit 52 includes diode 56 (connected to one side of capacitor 54), transistor 57, resistor 58 and an RC network (consisting of parallel connected resistor 59 and capacitor 60) for transistor turn-on (negative bleeder circuit 53 has the diode connected to one side of capacitor 55). Such a bleeder circuit turns on slightly whenever the voltage on the gate rises sufficiently to turn on the transistor. As soon as this voltage has charged the capacitor across the base of the bleeder transistor, the bleeder transistor will turn on sufficiently for capacitor discharge.

When two output capacitors (such as capacitors 54 and 55) are used, however, there is no complete DC path around the circuit to fully discharge the capacitors. If the capacitors become equally charged to a sufficient voltage, for example 20 volts, while circuits 52 and 53 would ensure that the voltages across these two capacitors were equal, circuits 52 and 53 could not actually dissipate the accumulated charge unless a DC path is provided.

In practice, charge sometimes gathers in these capacitors. This is important because small, compact ceramic capacitors lose their capacitance when the voltage across them is high. This causes the output pulses to have sloping top portions and even greater voltage across the capacitors. The charge problem is effectively corrected by including a high resistance shunt 62 across one of the two output capacitors, as illustrated in FIG. 9A. Only one of the output capacitors is shunted so that one capacitor remains in the output current path to ensure that the net DC delivered to the patient will be zero.

The skin of a user between spaced electrodes appears as a complex RC network which illustrates that, although the ohmic resistance path across the tissue may be high, it is nevertheless an ohmic path that can conduct DC charge around a circuit path to discharge both capacitors 54 and 55.

A bleeder circuit, such as shown in FIG. 9B, has another function. If the pulse width should become very long and/or the pulse amplitude should become very high, the bleeder circuit will turn on hard and actually short out the voltage across the two electrodes. This function serves as a safety device in the event that the logic circuitry fails and produces extremely long turn-on control pulses.

While a bleeder circuit such as illustrated in FIG. 9B can also include a diode positioned between the junction of resistor 59 and capacitor 60 and the junction of transistor 57 and electrode 33, such a diode operates, at least in part, as a clamp, and has been found to be undesirable for use with a biphasic output stage because a spike of current (handled by such a diode) will destroy the interphase delay that is necessary in the output stage.

A now preferred biphasic output stage is shown in FIG. 10, along with multiplexer 38. While only output stage 20 is shown, it is to be realized that output stage 21, as shown in FIG. 1, is preferably identical and is likewise connected with multiplexer 38.

As shown, output stage 20 includes capacitors 66 and 67 for capacitance coupling of the biphasic output pulses to electrodes 32 and 33, and capacitor 67 has a shunt resistor 68 connected thereacross. Control pulses are supplied to the output stage from microprocessor control unit 18 through multiplexor 38 which supplies control pulse outputs to both output stages 20 and 21.

Multiplexor 38 has a field effect transistor (FET) 70 connected with the enable control pulse input, has a resistor 72 connecting the drain of FET 70 to the Y input, and has a resistor 73 connecting the X input with the 5 volt power supply. The 5 volt level supplied to the multiplexer through the X input is used to switch on transistors 75 and 76.

The control pulses from the X2 and X3 outputs of multiplexor 38 (for channel A) are coupled to transistors 75 and 76 for level translation and signal inversion to ensure proper operation of the gate transistors (field effect transistors 78 and 79 as shown in FIG. 10). As indicated, transistors 75 and 76 have their emitters connected with ground through resistors 81 and 82 (to supply a fixed voltage drive to the associated FET despite changes in the high voltage supply), FET 78 has parallel connected resistor 84 and capacitor 85 connecting the gate of the FET with the high voltage (from converter 16) to turn off FET 78 when transistor 75 turns off, and FET 79 has parallel connected resistor 86 and capacitor 87 connecting the gate of the FET with the high voltage to turn off FET 79 when transistor 76 turns off. In addition, FETs 78 and 79 have diodes 89 and 90 connected in series with the drain of the FET to protect the FETs from conducting in the reverse direction.

As also shown in FIG. 10, output stage 20 includes dual transistorized bleeder circuits 92 and 93 that are polarized, and therefore operate properly only in one direction. Field effect transistors 95 and 96 are used in these circuits and each contains an internal shunt diode that makes them appear a short circuit when they are reverse biased. As shown, FET 95 of bleeder circuit 92 has a series connected diode 98 that prevents reverse currents from flowing, and FET 96 of bleeder circuit 93 has a series connected diode 99 that prevents reverse currents from flowing.

In addition, bleeder circuit 92 has resistor 101 and an RC circuit, consisting of resistor 102 connected in parallel with capacitor 103, connected with FET 95, and bleeder circuit 93 has resistor 105 and an RC circuit, consisting of resistor 106 connected in parallel with capacitor 107, connected with FET 96.

As also shown, FET 95 has a diode 109 connected in series with the source of FET 95, while FET 96 has a diode 110 connected in series with the source of FET 96.

Output stage, or channel, 20 is designed to operate in conjunction with output stage, or channel, 21. When one channel is operating, it is important that the other channel does not provide a return path to the high voltage supply or ground. This would destroy the isolation because currents would appear at electrodes without the direct control of the control pulses that is supposed to completely determine the currents at each electrode.

Primary isolation is provided by the timing of the control pulses. A two channel device providing biphasic stimulation of each channel has two biphasic output stages each of which is connectable to a pair of electrodes. Each stage is separately driven by control pulse pairs that are separated in time from the control pulses of the other channels, as shown in FIG. 2.

Monitoring diodes 112 and 113 are connected with variable-resistor/switch FETs 115 and 116 (which also have resistors 118 and 119 to ground connected therewith) so that these diodes detect when the drain voltages of the transistors are approaching saturation. These signals are used to boost the high voltage to keep the transistors out of saturation and the stimulator operating at maximum energy efficiency.

As shown, diodes 112 and 113 are connected between the FET 115 or 116) and the associated series protection diode (109 or 110), which diode prevents the associated FET from operating in the reverse direction. By this connection, the diodes cannot be forward biased by the opposite channel turning on, which would cause the high voltage supply to produce maximum voltage at all times.

Each output stage generates constant current rectangular biphasic output pulses. The source currents from all four intensity level control transistors (FETs 115 and 116 of output stage 20 as shown in FIG. 10 and like FETs for output stage 21) are brought together and passed through a common source to ground connected resistor 121. Since the currents through each half output stage are on at different times, the signals that appear across sense resistor 121 are unique for each half output stage.

The voltage across sense resistor 121 is fed to the negative input of operational amplifier 123 (a constant current amplifier that is connected with the 5 volt power supply with a by-pass capacitor 125 to ground connected thereto). The positive input to operational amplifier 123 is a reference voltage signal that represents the current level to be generated (and could be provided through a potentiometer, but is preferably generated by a digital-to-analog converter, as indicated in FIG. 1) with the reference voltage being coupled to the positive input through resistor 127 having a resistor 128 to ground connected therewith. The amplifier is stable because feedback from the output current is negative and causes the negative input voltage to become equal to (or at least closely approach) the positive reference voltage input. The output from operational amplifier 123 is coupled to the Y input of multiplexer 38. FET 70 and resistor 72 comprise a pull-up to improve the positive drive of operational amplifier 123.

In operation, the user turns on the device by depressing briefly on/increase intensity switch 25. The user then adjusts the intensity to the desired degree of stimulation by depressing either on/increase switch 25 or off/decrease switch 26 and observing the LED light array at intensity display 23. For continuous stimulation this is all that is necessary until treatment is terminated by decreasing stimulation to minimum (zero) by actuating decrease switch 26 until all display LED lights are off.

For a programmed treatment cycle, timed treatment switch 28 is depressed briefly, and a second LED at the minimum indication end of the LED array will be energized and will blink indicating that the device is in a standby condition with no stimulation provided.

To begin treatment, timed treatment switch 28 is again depressed briefly to commence the automatic treatment cycle according to the algorithm as shown in FIG. 6, with the level of stimulation being indicated at intensity display 23 by the blinking light (as brought out above, the blinking light is moved toward the continuous light to eventually merge with the continuous light to indicate that the desired level of stimulation has been reached, and near the end of the treatment, the blinking light will again be moved toward the minimum intensity level with the blinking light reaching the minimum level when stimulation ends to indicate the device is again in the standby condition). If the device is not manually turned off, the device will automatically turn off if a new treatment is not initiated within eight hours.

As can be appreciated from the foregoing, this invention provides an improved electronic stimulating device and, more particularly, an improved transcutaneous stimulating device, having a timed treatment of varying intensity of stimulation, along with a display of selected and applied intensities, and a method for effecting a timed treatment of varying intensities of stimulation.

What is claimed is:

1. An electronic stimulating device for providing electrical stimulation at automatically varied intensities, said device comprising:
   generating means for generating electrical stimulation the intensity of which is variable, said generating means providing said generated electrical stimulation as an output signal suitable for application to a user receiving said output signal;
   control means connected with said generating means for automatically controlling the intensity of said generated electrical stimulation, said control means causing said generated electrical stimulation to be progressively increased during first and second successive time periods with substantially the entire range of levels of intensities of said generated electrical stimulation being lower during said first period relative to substantially the entire range of levels of intensities of said generated electrical stimulation during said second period, and with the rate of increase of intensity during said first period being different from the rate of increase of intensity during said second period; and
   actuating means connected with said control means to institute said automatic control of said intensity by said control means.

2. The device of claim 1 wherein said control means causes one of said ranges of levels of intensity of said generated electrical stimulation occurring during said first and second time periods to include the sensory threshold level of a user receiving said output signal.

3. The device of claim 2 wherein said control means causes said first time period to include the sensory threshold level of a user receiving said output signal, and said second time period to be suitable for user accommodation purposes.

4. The device of claim 1 wherein said control means causes an abrupt increase in intensity preceding said first time period.

5. The device of claim 1 wherein said control means automatically terminates said generated electric stimulation after generation of said electrical stimulation at full intensity during a third time period following said second time period.

6. The device of claim 5 wherein said control means causes said termination of said generated electrical stimulation to include a fourth time period during which the intensity is progressively decreased, with said fourth time period including the sensory threshold level of a user receiving said output signal.

7. The device of claim 6 wherein said control means causes said intensity to be abruptly dropped to zero after said fourth time period.

8. The device of claim 1 wherein said device includes display means for displaying an indication of at least one of a selected full intensity of generated electrical stimulation and the intensity of said electrical stimulation.

9. The device of claim 8 wherein said display means provides an indication of both said selected full intensity and the intensity then being generated when said intensities are different.

10. The device of claim 9 wherein said display means is a visual display one portion of which is a continuous indication and the other portion of which is an intermittent indication.

11. The device of claim 10 wherein said display means includes indications of maximum and minimum levels with said visual display extending therebetween.

12. The device of claim 11 wherein said visual display is a lighted display that includes a row of light emitting diodes the selective energization of which is indicative of said selected and generated intensities.

13. An electronic stimulating device for providing electrical stimulation at automatically varied intensities, said device comprising:
generating means for generating electrical stimulation the intensity of which is variable, said generating means providing said generated electrical stimulation as an output signal suitable for application to a user receiving said output signal;
control means connected with said generating means for automatically controlling the intensity of said generated electrical stimulation, said control means causing said generated electrical stimulation to be progressively increased during first and second successive time periods with the range of levels of intensities of said generated electrical stimulation being lower during said first period relative to the range of levels of intensities of said generated electrical stimulation during said second period, with said first time period including the sensory threshold level of a user receiving said output signal, with said second time period being suitable for user accommodation purposes, and with said intensity of said generated electrical stimulation during said first time period being increased at a rate that is greater than the rate of intensity increase of said generated electrical stimulation during said second time period; and
actuating means connected with said control means to institute said automatic control of said intensity by said control means.

14. An electronic stimulating device for providing electrical stimulation at automatically varied intensities, said device comprising:
generating means for generating electrical stimulation the intensity of which is variable, said generating means providing said generated electrical stimulation as an output signal suitable for application to a user receiving said output signal;
control means connected with said generating means for automatically controlling the intensity of said generated electrical stimulation, said control means causing said generated electrical stimulation to be initially applied and abruptly increased to a first predetermined level below the sensory threshold of a user receiving said output signal during a first time period, with the intensity being caused to be progressively increased to a second predetermined level above the sensory threshold level of a user receiving said output signal during a second time period following said first time period, and with the intensity being caused to be progressively increased to a full predetermined level during a third time period following said second time period, with the rate of increase during said third time period being less than the rate of intensity increase during said second time period; and
actuating means connected with said control means to initiate said automatic control of said intensity by said control means.

15. The device of claim 14 wherein said control means causes said first predetermined level of generated electrical stimulation to be about fifty percent of full intensity, and causes said second predetermined level to be about ninety percent of full intensity.

16. The device of claim 15 wherein said control means causes said second time period to extend for about one second, and said third time period to extend for about five minutes.

17. The device of claim 14 wherein said control means causes said electrical stimulation to be generated at full selected intensity during a fourth time period, and causes termination of said generated electrical stimulation during fifth and sixth successively occurring time periods following said fourth time period, with the intensity during said fifth time period being caused to be progressively reduced from full intensity to an intensity level less than the threshold level of a user receiving said output signal, and with the intensity being caused to be abruptly dropped to zero during said sixth time period.

18. The device of claim 17 wherein said control means causes said intensity to be progressively reduced to about fifty percent of full intensity during said fifth time period, with said fifth time period being caused to extend for about seven and one-half minutes.

19. The device of claim 14 wherein said generating means provides generated electrical stimulation as an output signal suitable for therapeutic stimulation as an output signal suitable for therapeutic purposes.

20. The device of claim 14 wherein said device is a transcutaneous nerve stimulating device and said output signal is suitable for effecting suppression of pain.

21. In an electronic stimulating device having generating means for generating electrical stimulation and control means for varying the intensity of said generated electrical stimulation, a display unit, comprising:
first indicating means capable of providing separate simultaneous indications based upon the then generated electrical stimulation and a selected full intensity level of electrical stimulation to be generated; and
second indicating means, cooperable with said first indicating means, indicating the level of said then generated electrical stimulation and said selected level of said full intensity of electrical stimulation to be generated to thereby enable a simultaneous display of said then generated electrical stimulation and said selected level of full intensity of electrical stimulation to be generated when different from one another.

22. The unit of claim 21 wherein said second indicating means includes indicia indicating at least minimum and maximum levels, and wherein said first indicating means is a visual indicator providing said separate simultaneous indications through use of a continuous light and a blinking light.

23. The unit of claim 22 wherein said first indicating means includes a plurality of light emitting diodes arranged in a row between said minimum and maximum indicators of said second indicating means, with a light emitting diode when energized continuously being indicative of a selected full intensity level to be generated, and with a different one of said light emitting diodes when repeatedly energized and de-energized being indicative of an applied intensity level that is different from that of said selected full intensity level to be generated.

24. A method for providing electrical stimulation to a user, said method comprising:
applying electrical stimulation to a user during a first time period at progressively increasing levels of stimulation;
applying electrical stimulation to a user during a second time period, following said first time period, at progressively increasing levels of stimulation different from the progressively increasing levels of stimulation applied during the first time period, with substantially the entire range of levels of stimulation applied during the second time period being greater than substantially the entire range of levels of stimulation applied during said first time period, and with said applied stimulation reaching a selected full level at the end of said second time period;
applying electrical stimulation at said selected full intensity level during a third time period; and
terminating application of electrical stimulation to the user after the end of the third time period.

25. The method of claim 24 wherein said method includes applying electrical stimulation at the sensory threshold level of the user during one portion of application of stimulation at progressively increasing levels during one of said first and second time periods.

26. The method of claim 24 wherein said method includes initially applying stimulation to a user and abruptly increasing the intensity prior to application of intensity to the user during said first time period.

27. The method of claim 24 wherein said step of terminating application of stimulation includes decreasing the intensity of stimulation during a fourth time period to a level below the sensory threshold level of the user, and then abruptly dropping the intensity to zero.

28. The method of claim 24 wherein said method includes displaying the then applied level of intensity and the selected full level of intensity to be applied when different from the then applied level of intensity.

29. The method of claim 28 wherein said step of displaying said then applied level of intensity and said selected full level of intensity to be applied includes providing a visual display with two indicators one of which is indicative of said then applied level of intensity and the other of which is indicative of said selected full intensity level to be applied.

30. The method of claim 29 wherein said stop of providing a visual display having two indicators is effected by providing a continuous light as one indicator and a blinking light as the other indicator.

31. A method for providing electrical stimulation to a user, said method comprising:
applying electrical stimulation to a user during a first time period at progressively increasing levels of stimulation with application of said stimulation being at the sensory threshold level of the user during a portion of said first time period;
applying electrical stimulation to a user during a second time period, following said first time period, at progressively increasing levels of stimulation, with the levels of stimulation applied during second time period being greater than the levels of stimulation applied during said first time period, with application of said stimulation during said second time period being for user accommodation purposes, and with said applied stimulation reaching a selected full level at the end of said second time period;
applying electrical stimulation at said selected full intensity level during a third time period; and
terminating application of electrical stimulation to the user after the end of the third time period.

32. The method of claim 31 wherein said method includes applying stimulation during said first time period at a rate of increase greater than the rate of increase of applied stimulation during said second time period.

33. A method for providing electrical stimulation to a user at automatically varied intensities, said method comprising:
generating electrical stimulation the intensity of which is variable;
applying the stimulation to a user at near zero intensity and then abruptly increasing the intensity of the stimulation to a first predetermined intensity level that is below the sensory threshold level of the user during a first time period;
increasing the intensity level applied to the user during a second time period to a second predetermined intensity level that is above the sensory threshold level of the user with the rate of increase of intensity being less than the rate of increase during the first time period;
increasing the intensity level applied to the user during a third time period to a third predetermined intensity level that is equal to a selected full intensity level to be applied to the user with the rate of increase during said third period being less than the rate of increase during the second time period;
applying stimulation to the user at the selected full intensity level during a fourth time period; and
decreasing the intensity level of stimulation to zero during fifth and sixth time periods following said fourth time period with said intensity being decreased during said fifth time period to a level below the sensory threshold level of the user and thereafter abruptly decreased to zero during said sixth time period, and with the rate of decrease during said fifth time period being slow relative to said abrupt decrease in intensity that occurs during said sixth time period.

34. The method of claim 33 wherein said intensity is abruptly increased to about fifty percent of full intensity during said first time period, wherein said intensity is increased during said second time period from about fifty percent of full intensity to about ninety percent of full intensity during a time of about one second, and wherein said intensity is increased during said third time period from about ninety percent of full intensity to full intensity during a time of about five minutes.

35. The method of claim 33 wherein said stimulation at said selected full intensity is applied during said fourth time period for about twenty-five minutes.

36. The method of claim 33 wherein said intensity is decreased during said fifth time period to about fifty percent during a time of about seven and one-half minutes.

* * * * *